United States Patent
Mutilangi et al.

(10) Patent No.: US 10,426,181 B2
(45) Date of Patent: Oct. 1, 2019

(54) METHOD FOR PREPARING HIGH ACID RTD WHOLE GRAIN BEVERAGES

(75) Inventors: William Mutilangi, Peekskill, NY (US); Ricardo Pereyra, White Plains, NY (US)

(73) Assignee: The Quaker Oats Company, Chicago, IL (US)

( * ) Notice: Subject to any disclaimer, the term of this patent is extended or adjusted under 35 U.S.C. 154(b) by 374 days.

(21) Appl. No.: 13/414,184

(22) Filed: Mar. 7, 2012

(65) Prior Publication Data

US 2012/0244249 A1    Sep. 27, 2012

Related U.S. Application Data

(60) Provisional application No. 61/454,726, filed on Mar. 21, 2011.

(51) Int. Cl.
*A23L 2/52* (2006.01)
*A23L 7/104* (2016.01)

(52) U.S. Cl.
CPC .............. *A23L 2/52* (2013.01); *A23L 7/107* (2016.08)

(58) Field of Classification Search
USPC ....... 426/330, 330.2, 330.3, 330.5, 580, 590
See application file for complete search history.

(56) References Cited

U.S. PATENT DOCUMENTS

| | | |
|---|---|---|
| 1,163,175 A | 12/1915 | Rullman |
| 1,384,894 A | 7/1921 | Horlick |
| 2,999,018 A | 9/1961 | Huffman |
| 3,116,150 A | 12/1963 | Baker |
| 3,317,402 A | 5/1967 | Smith |
| 3,391,003 A | 7/1968 | Armstrong |
| 3,494,769 A | 2/1970 | Tressler |
| 3,579,352 A | 5/1971 | Bookwalter |
| 3,595,671 A | 7/1971 | Cooke |
| 3,732,109 A | 5/1973 | Poat |
| 3,753,728 A | 8/1973 | Bedenk |
| 3,851,085 A | 11/1974 | Rodgers |
| 3,869,558 A | 3/1975 | Hampton |
| 3,925,343 A | 12/1975 | Hampton |
| 3,950,543 A | 4/1976 | Buffa |
| 3,958,016 A | 5/1976 | Galle |
| 4,028,468 A | 6/1977 | Hohner |
| 4,038,427 A | 7/1977 | Martin |
| 4,041,187 A | 8/1977 | Nelson |
| 4,167,584 A | 9/1979 | Nelson |
| 4,171,384 A | 10/1979 | Chwalek |
| 4,247,561 A | 1/1981 | Nelson |
| 4,259,358 A | 3/1981 | Duthie |
| 4,266,027 A | 5/1981 | Muller |
| 4,282,319 A | 8/1981 | Conrad |
| 4,330,625 A | 5/1982 | Miller |
| 4,377,602 A | 3/1983 | Conrad |
| 4,431,674 A | 2/1984 | Fulger |
| 4,435,429 A | 3/1984 | Burrows |
| 4,435,430 A | 3/1984 | Fulger |
| 4,438,150 A | 3/1984 | Gantwerker |
| 4,439,460 A | 3/1984 | Tsau |
| 4,500,558 A | 2/1985 | Fulger |
| 4,551,347 A | 11/1985 | Karwowski |
| 4,613,507 A | 9/1986 | Fulger |
| 4,656,040 A | 4/1987 | Fulger |
| 4,668,519 A | 5/1987 | Dartey |
| 4,692,340 A | 9/1987 | Grutte |
| 4,710,386 A | 12/1987 | Fulger |
| 4,777,056 A | 10/1988 | Buhler |
| 4,814,172 A | 3/1989 | Chavkin |
| 4,834,988 A | 5/1989 | Karwowski |
| 4,834,989 A | 5/1989 | Bolles |
| 4,886,665 A | 12/1989 | Kovacs |
| 4,894,242 A | 1/1990 | Mitchell |
| 4,957,563 A | 9/1990 | Gallaher |
| 4,996,063 A * | 2/1991 | Inglett .............................. 426/21 |
| 4,999,298 A | 3/1991 | Wolfe |
| 5,021,248 A | 6/1991 | Stark |
| 5,045,328 A | 9/1991 | Lewis |
| 5,106,343 A | 4/1992 | Laufer |
| 5,106,634 A | 4/1992 | Thacker |
| 5,145,698 A | 9/1992 | Cajigas |
| 5,234,704 A | 8/1993 | Devine |
| 5,320,856 A | 6/1994 | Veronesi |
| 5,334,407 A | 8/1994 | Donnelly |
| 5,346,890 A | 9/1994 | Hagiwara |
| 5,385,746 A | 1/1995 | De Almeida |
| 5,395,623 A | 3/1995 | Kovach |
| 5,407,694 A * | 4/1995 | Devine et al. ................. 426/565 |
| 5,458,893 A | 10/1995 | Smith |
| 5,464,760 A | 11/1995 | Tsai |
| 5,476,675 A | 12/1995 | Lou |
| 5,490,997 A * | 2/1996 | Devine et al. ................. 426/573 |
| 5,523,109 A | 6/1996 | Hellweg |
| 5,554,402 A | 9/1996 | Smith |
| 5,571,334 A | 11/1996 | Dunn |
| 5,593,503 A | 1/1997 | Shi |
| 5,656,317 A | 8/1997 | Smits |
| 5,686,123 A | 11/1997 | Lindahl |
| 5,744,187 A | 4/1998 | Gaynor |
| 5,846,786 A | 12/1998 | Senkeleski |
| 5,849,090 A | 12/1998 | Haralampu |
| 5,863,590 A | 1/1999 | Alan |
| 5,888,548 A | 3/1999 | Wongsuragrai |

(Continued)

FOREIGN PATENT DOCUMENTS

| | | |
|---|---|---|
| AU | 1989045913 | 12/1989 |
| CA | 1045890 | 1/1979 |

(Continued)

OTHER PUBLICATIONS

International Search Report and Written Opinion from related PCT/US2012/026110 dated Jun. 13, 2012.

(Continued)

*Primary Examiner* — Tamra L. Dicus
(74) *Attorney, Agent, or Firm* — Barnes & Thornburg LLP; G. Peter Nichols

(57) ABSTRACT

A method for preparing a low viscosity whole grain flour slurry including hydrating whole grain flour in water heated at a temperature of 87 to 99° C., cooling the mixture, adding an enzyme to reduce the viscosity, and acidifying the flour-water mixture to reduce the pH to obtain a reduced viscosity whole grain flour slurry.

11 Claims, No Drawings

(56) References Cited

U.S. PATENT DOCUMENTS

| | | | |
|---|---|---|---|
| 5,912,031 A | 6/1999 | Fitchett | |
| 5,932,264 A | 8/1999 | Hurd | |
| 5,962,047 A | 10/1999 | Gross | |
| 5,981,237 A | 11/1999 | Meagher | |
| 5,985,339 A | 11/1999 | Kamarei | |
| 5,997,917 A | 12/1999 | Uchida | |
| 6,013,289 A | 1/2000 | Blank | |
| 6,054,302 A | 4/2000 | Shi | |
| 6,135,015 A | 10/2000 | Mendez | |
| 6,168,821 B1 | 1/2001 | Castleberry | |
| 6,190,708 B1 | 2/2001 | Triantafyllou | |
| 6,210,722 B1 | 4/2001 | Wullschleger | |
| 6,210,738 B1 | 4/2001 | Chen | |
| 6,210,741 B1 | 4/2001 | Van Lengerich | |
| 6,221,406 B1 | 4/2001 | Meschonat | |
| 6,244,528 B1 | 6/2001 | Wallis | |
| 6,277,186 B1 | 8/2001 | Shi | |
| 6,287,621 B1 | 9/2001 | LaCourse | |
| 6,287,626 B1 | 9/2001 | Fox | |
| 6,387,435 B1 | 5/2002 | Fox | |
| 6,395,314 B1 * | 5/2002 | Whalen et al. | 426/28 |
| 6,451,369 B1 | 9/2002 | Triantafyllou | |
| 6,468,355 B1 | 10/2002 | Thompson | |
| 6,482,459 B1 | 11/2002 | Anderson | |
| 6,485,575 B2 | 11/2002 | Yuan | |
| 6,551,366 B1 | 4/2003 | D'Souza | |
| 6,592,914 B1 | 7/2003 | Triantafyllou | |
| 6,610,349 B1 | 8/2003 | Delrue | |
| 6,617,446 B1 | 9/2003 | Papadopoulos | |
| 6,685,974 B2 | 2/2004 | Whalen | |
| 6,720,022 B1 | 4/2004 | Amaut | |
| 6,723,358 B1 | 4/2004 | Van Lengerich | |
| 6,737,099 B2 | 5/2004 | Guraya | |
| 6,759,077 B1 | 7/2004 | Lewis | |
| 6,797,307 B2 | 9/2004 | Malkki | |
| 7,030,092 B1 | 4/2006 | Levine | |
| 7,037,704 B2 | 5/2006 | Dunn-Coleman | |
| 7,101,585 B2 | 9/2006 | Shen | |
| 7,138,519 B2 | 11/2006 | Morgan | |
| 7,160,564 B2 | 1/2007 | Oste | |
| 7,244,457 B2 | 7/2007 | Racicot | |
| 7,419,694 B2 | 9/2008 | Korolchuk | |
| 7,678,403 B2 | 3/2010 | Mitchell | |
| 7,754,270 B2 | 7/2010 | Wuersch | |
| 7,794,774 B2 | 9/2010 | Foster | |
| 7,914,972 B2 | 3/2011 | Fujiwara | |
| 8,241,696 B2 | 8/2012 | Chung | |
| 8,518,469 B2 | 8/2013 | MacDonald | |
| 8,574,644 B2 | 11/2013 | Chatel | |
| 8,591,970 B2 | 11/2013 | Chatel | |
| 8,742,095 B2 | 6/2014 | Lehtomaki | |
| 8,962,046 B2 | 2/2015 | Malkki | |
| 9,149,060 B2 | 10/2015 | Chatel | |
| 9,150,895 B2 | 10/2015 | Kurihara | |
| 9,433,236 B2 | 9/2016 | Kaukovita-Norja | |
| 2001/0002269 A1 | 5/2001 | Zhao | |
| 2001/0022986 A1 | 9/2001 | Girsh | |
| 2002/0127319 A1 | 9/2002 | Gare | |
| 2002/0187224 A1 | 12/2002 | Haefliger | |
| 2003/0091716 A1 | 5/2003 | Kuramoto | |
| 2003/0124195 A1 | 7/2003 | Delprato | |
| 2003/0170362 A1 | 9/2003 | Manning | |
| 2004/0028797 A1 | 2/2004 | Squire | |
| 2004/0101935 A1 * | 5/2004 | Vasanthan et al. | 435/101 |
| 2004/0140584 A1 | 7/2004 | Wang | |
| 2004/0151805 A1 | 8/2004 | Gao | |
| 2004/0219261 A1 | 11/2004 | Triantafyllou | |
| 2004/0258829 A1 | 12/2004 | Zheng | |
| 2005/0064080 A1 | 3/2005 | Creighton | |
| 2005/0089602 A1 | 4/2005 | Kvist | |
| 2005/0106216 A1 | 5/2005 | Maurer | |
| 2005/0181114 A1 | 8/2005 | Bruemmer | |
| 2005/0191400 A1 | 9/2005 | Satyavolu | |
| 2005/0214347 A1 | 9/2005 | Astrup | |
| 2005/0233051 A1 | 10/2005 | Shen | |
| 2005/0244563 A1 | 11/2005 | Cavalieri | |
| 2005/0260305 A1 | 11/2005 | Adele | |
| 2006/0008574 A1 | 1/2006 | Begli | |
| 2006/0013940 A1 | 1/2006 | Mueller | |
| 2006/0093720 A1 | 5/2006 | Tatz | |
| 2006/0115573 A1 | 6/2006 | Singer | |
| 2006/0121174 A1 | 6/2006 | Franke | |
| 2006/0134299 A1 | 6/2006 | Lahteenmaki | |
| 2006/0141097 A1 | 6/2006 | Guo | |
| 2006/0240148 A1 | 10/2006 | Nguyen | |
| 2006/0251791 A1 | 11/2006 | Rubio | |
| 2006/0257548 A1 | 11/2006 | Crofsky | |
| 2006/0280838 A1 | 12/2006 | Kvist | |
| 2006/0286269 A1 | 12/2006 | Shah | |
| 2007/0026105 A1 | 2/2007 | Seo | |
| 2007/0059340 A1 | 3/2007 | Bello | |
| 2007/0071857 A1 | 3/2007 | Vemuganti | |
| 2007/0141218 A1 | 6/2007 | Chatel | |
| 2007/0154609 A1 | 7/2007 | Li | |
| 2007/0172568 A1 | 7/2007 | Spelman | |
| 2007/0178199 A1 | 8/2007 | Minor | |
| 2007/0184175 A1 | 8/2007 | Rubio | |
| 2007/0212472 A1 | 9/2007 | Hoelstein | |
| 2007/0243301 A1 | 10/2007 | Barnett | |
| 2007/0264400 A1 | 11/2007 | Milne | |
| 2007/0292583 A1 | 12/2007 | Haynes | |
| 2008/0003340 A1 | 1/2008 | Karwowski | |
| 2008/0008801 A1 | 1/2008 | Bamekow | |
| 2008/0098900 A1 | 5/2008 | Aremu | |
| 2008/0131582 A1 | 6/2008 | Karwowski | |
| 2008/0171114 A1 | 7/2008 | Castillo Rodriguez | |
| 2008/0260909 A1 | 10/2008 | Chung | |
| 2008/0305212 A1 | 12/2008 | Wong | |
| 2009/0053771 A1 | 2/2009 | Dale | |
| 2009/0148562 A1 | 6/2009 | Lin | |
| 2009/0181128 A1 | 7/2009 | Blumenthal | |
| 2009/0221041 A1 | 9/2009 | Aux | |
| 2009/0253191 A1 | 10/2009 | Ward | |
| 2009/0311376 A1 | 12/2009 | Rao | |
| 2010/0015306 A1 * | 1/2010 | Pereyra | 426/330.2 |
| 2010/0104718 A1 | 4/2010 | Durand | |
| 2010/0112127 A1 * | 5/2010 | Chatel et al. | 426/29 |
| 2010/0112167 A1 | 5/2010 | Chatel | |
| 2010/0178400 A1 | 7/2010 | Pereyra | |
| 2010/0189870 A1 | 7/2010 | Frohberg | |
| 2010/0316765 A1 * | 12/2010 | French et al. | 426/28 |
| 2011/0009613 A1 | 1/2011 | Kaukovirta-Norja | |
| 2011/0020523 A1 | 1/2011 | Pereyra et al. | |
| 2012/0082740 A1 | 4/2012 | Collins | |
| 2012/0245111 A1 | 9/2012 | Hoebler | |
| 2013/0017300 A1 | 1/2013 | Avila | |
| 2013/0183405 A1 | 7/2013 | Chatel | |
| 2013/0209610 A1 | 8/2013 | Carder | |
| 2013/0323799 A1 | 12/2013 | Takaha | |
| 2014/0017356 A1 | 1/2014 | Te Biesebeke | |
| 2014/0050819 A1 | 2/2014 | Chatel | |
| 2014/0087430 A1 | 3/2014 | Lee | |
| 2014/0170723 A1 | 6/2014 | Dobson | |
| 2014/0193563 A1 | 7/2014 | Carder | |
| 2014/0193564 A1 | 7/2014 | Carder | |
| 2015/0183821 A1 | 7/2015 | Konstantinov | |
| 2015/0191758 A1 | 7/2015 | Larsen | |
| 2015/0351432 A1 | 12/2015 | Triantafyllou | |
| 2016/0185641 A1 | 6/2016 | Zuback | |

FOREIGN PATENT DOCUMENTS

| | | |
|---|---|---|
| CA | 2015149 | 10/1990 |
| CN | 1386446 A | 12/2002 |
| CN | 1153524 C | 6/2004 |
| DE | 970141 C | 8/1958 |
| EP | 0078782 B1 | 5/1983 |
| EP | 0312220 A1 | 4/1989 |
| EP | 0512249 A1 | 11/1992 |
| EP | 0231729 B1 | 8/1993 |
| EP | 0634106 A1 | 1/1995 |
| EP | 0474230 B1 | 3/1995 |
| EP | 1723853 A2 | 11/2006 |
| EP | 1782697 A2 | 5/2007 |

(56) References Cited

FOREIGN PATENT DOCUMENTS

| EP | 1872666 A1 | 1/2008 |
|---|---|---|
| EP | 1123012 B1 | 1/2011 |
| FR | 2620906 A1 | 3/1989 |
| GB | 1168692 A | 10/1969 |
| JP | S63116657 | 5/1988 |
| JP | 2000004852 | 1/2000 |
| JP | 2002171920 | 6/2002 |
| JP | 2002-527089 A | 8/2002 |
| JP | 2009207359 A | 9/2009 |
| JP | 2010-051285 A | 3/2010 |
| JP | 2010-517573 A | 5/2010 |
| RU | 2044503 C1 | 9/1995 |
| RU | 2237149 | 10/2004 |
| WO | 1992010106 A2 | 6/1992 |
| WO | 1993000826 A1 | 1/1993 |
| WO | 1994013826 A1 | 6/1994 |
| WO | 1996004799 A1 | 2/1996 |
| WO | 0022938 | 4/2000 |
| WO | 2000030457 A1 | 6/2000 |
| WO | 2003011052 A1 | 2/2003 |
| WO | 2003090557 A1 | 11/2003 |
| WO | 2007020059 A1 | 2/2007 |
| WO | WO 2008/097620 A1 | 8/2008 |
| WO | 2009127687 A1 | 10/2009 |
| WO | 2009158588 A1 | 12/2009 |
| WO | 2010008677 | 1/2010 |
| WO | 2014160351 A1 | 10/2014 |

OTHER PUBLICATIONS

Notification of the Second Office Action for CN Appl. No. 201280021109.2, dated Dec. 2, 2014, The State Intellectual Property Office of the People's Republic of China, Beijing, China, 9 pages.
Notification of the Third Office Action for CN Appl. No. 201280021109.2, dated May 27, 2015, The State Intellectual Property Office of the People's Republic of China, Beijing, China, 3 pages.
Notification of the Fourth Office Action for CN Appl. No. 201280021109.2, dated Oct. 29, 2015, The State Intellectual Property Office of the People's Republic of China, Beijing, China, 8 pages.
Communication pursuant to Article 94(3) EPC for EP Appl. No. 12710819.9, dated Jul. 8, 2014, European Patent Office, Munich, Germany, 5 pages.
Notice of Grounds for Rejection for JP Appl. No. 2014-501081, dated for drafting Feb. 13, 2015, Japanese Patent Office, Tokyo, Japan, 3 pages.
Decision of Rejection for JP Appl. No. 2014-501081, dated for drafting Oct. 16, 2015, Japanese Patent Office, Tokyo, Japan, 3 pages.
Decision on Grant for RU Appl. No. 2013146708/13(072557), dated Dec. 3, 2014, Rospatent, Federal Institute of Industrial Property, Moscow, Russian Federation, 7 pages.
English Translation of Notification of the Second Office Action for CN Appl. No. 201280021109.2, dated Dec. 2, 2014, The State Intellectual Property Office of the People's Republic of China, Beijing, China, 7 pages.
English Translation of Notification of the Third Office Action for CN Appl. No. 201280021109.2, dated May 27, 2015, The State Intellectual Property Office of the People's Republic of China, Beijing, China, 3 pages.
English Translation of Notification of the Fourth Office Action for CN Appl. No. 201280021109.2, dated Oct. 29, 2015, The State Intellectual Property Office of the People's Republic of China, Beijing, China, 10 pages.
English Translation of Notice of Grounds for Rejection for JP Appl. No. 2014-501081, dated for drafting Feb. 13, 2015, Japanese Patent Office, Tokyo, Japan, 3 pages.
English Translation of Decision of Rejection for JP Appl. No. 2014-501081, dated for drafting Oct. 16, 2015, Japanese Patent Office, Tokyo, Japan, 3 pages.

English Translation of Decision on Grant for RU Appl. No. 2013146708/13(072557), dated Dec. 3, 2014, Rospatent, Federal Institute of Industrial Property, Moscow, Russian Federation, 4 pages.
Notice of Acceptance for AU Appl. No. 2012231653, dated Oct. 31, 2014, IP Australia, Sydney, Australia, 2 pages.
Requisition by the Examiner for CA Appl. No. 2,830,966, dated Sep. 10, 2014, Canadian Intellectual Property Office, Quebec, Canada, 2 pages.
Notice of Acceptance for CA Appl. No. 2,830,966, dated May 20, 2015 Canadian Intellectual Property Office, Quebec, Canada, 1 page.
Communication pursuant to Article 94(3) EPC for EP Appl. No. 12710819.9, dated May 11, 2015, European Patent Office, Munich, Germany, 6 pages.
Result of Consultation for EP Appl. No. 12710819.9, dated May 26, 2015, European Patent Office, Munich, Germany, 6 pages.
Communication under Rule 71(3) EPC for EP Appl. No. 12710819.9, dated Jul. 3, 2015, European Patent Office, Munich, Germany, 6 pages.
Summons to attend oral proceedings pursuant to Rule 115(1) EPC for EP Appl. No. 12710819.9, dated Feb. 12, 2015, European Patent Office, Munich, Germany, 5 pages.
Hao, L., *Food Additives*, $1^{st}$ edition, pp. 246-247, China Agricultural University Press, China (Aug. 2002).
Australian Patent Application No. 2012231653 Office Action dated Apr. 3, 2014.
Chinese Patent Application No. 201280021109.2 Office Action dated Jun. 23, 2014.
Notification of Reexamination for CN Appl. No. 201280021109,2, dated Dec. 14, 2016, The State Intellectual Property Office of the People's Republic of China, Beijing, China, 5 pages.
English Translation of Notification of Reexamination for CN Appl. No. 201280021109.2, dated Dec. 14, 2016, The State Intellectual Property Office of the People's Republic of China, Beijing, China, 10 pages.
Li, Z., et al. "Fermented food technology," China Metrology Publishing House, p. 141 (2012).
Zheng, B., "Food Enzymology," Southeast University Press, p. 132 (2006).
Anderson, et al. "Gelatinazation of corn grits by roll cooking, extrusion cooking and steaming," Staerke 22:130-135.
Anonymous: "Ovsena nahradka mlieka," XP002561727, URL:http://web.archive.org/web/20084200751511/http://www.aspsk.sk/ovsene_mlieko.htm>, retrieved from the internet on Dec. 18, 2009, pp. 1-1, dated Apr. 20, 2008.
Anonymous: ""Goldkill Instant Barley Drink"", XP002561728, URL:http:f/web.archive.org/web/20060303003347/goldkill.\ | com/goldkili_instant.php>, retrieved from the Internet on Dec. 28, 2009, pp. 1-2, dated Mar. 3, 2006.
Brenda, The comprehensive Enzyme Information System, BC 3.2.1.1.—alpha amylase; pp. 1 to 297; Retrieved from the internet: http://www.brenda-enzymes.info/php/result_flat.php4?ecno=3.2.1.1 &organism_list=,date unknown.
Camire, Mary Ellen, et al.""Thermal Processing Effects on Dietary Fiber Composition and Hydration Capacity in Corn Meal, Oat Meal, and Potato Peels,"" Cereal Chemistry 68(6),pp. 645-647, vol. 68,No. 6, 1991 (3 pages).
Changquing, Wang, et al, Study on the Extruding Production Method of Soluble Oats Fiber, vol. 28, No. 2, pp. 45-48, dated Mar. 20, 2002, with English Abstract.
Davis, "The Effect of Cold on Micro-Organisms in Relation to Dairying," Express Dairy Co (London), Proceedigns of the Society for Applied Bacteriology, vol. 14, Issue 2, pp. 216-242, Oct. 1951.
Moncel, Bethany, Food Reference, About.com "Why Does Milk Curdle," http://foodreference.about.com/od/Dairy/a/Why-Does-Milk-Curdle.htm, pp. 1-2 (2 pages).
Grenus, Food Product Design, Applications, Agglomerations, Jul. 10, 2014, Weeks Publishing Co., pp. 1-4, www.foodproductdesign.com/articles/2004/07/food-product-design-applications.
Gualberto, D.G. et al., Effect of extrusion processing on the soluble and insoluble fiber, and phytic acid contents of cereal brans, dated Sep. 28, 1997.

(56) References Cited

OTHER PUBLICATIONS

Gutkoski, L.C., et al., "Effect of Extrusion Process Variables on Physical and Chemical Properties of Extruded Oat Products", Plant Foods for Human Nutrition,© 2000 Kluwer Academic Publishers, pp. 315-325, dated Dec. 31, 1999.
Hoseney, R. Carl, ""Principles of Cereal Science and Technology,"" 1986, American Association of Cereal Chemists, Inc., St. Paul Minnesota 55121,pp. 148-149 (4 pages).
Inglett, G.E. et al., Oat beta-glucan-amylodextrin: Preliminary preparations and biological properties, plant Fd. For Human Nutrition, vol. 45, pp. 53-61, dated Jun. 5, 2012.
Likimani, T.A., "Extrusion Cooking of Corn/Soybean Mix in Presence of Thermostable a-Amylase", Jounal of Food Science, vol. 56, No. 1, 1991, pp. 99-105 (7 pages).
Linko Y Y et al: The effect of HTST-extrusion on retention of cereal alpha-amylase activity and on enzymatic hydrolisis of barley starch, Food Processing Systems, Applied Science Publ, UK, Jan. 1, 1980 (Jan. 1, 1980), pp. Abstr, 4.2.25, 210-223, XP009127925, ISBN: 978-0-85334-896-2.
PCT Application No. PCT/US2008/060323 International Search Report and Written Opinion dated Aug. 13, 2008.
PCT Application No. PCT/US2009/059916 International Search Report and Written Opinion dated Feb. 16, 2010.
PCT Application No. PCT/US2009/060016, ISR, dated Feb. 8, 2010.
PCT Application No. PCT/US2009/060016, IPRP-WO, dated May 19, 2011.
PCT Application No. PCT/US2010/038506 International Search Report and Written Opinion dated Aug. 10, 2010, 18 pages.
PCT Application No. PCT/US2012/046450 International Search Report and Written Opinion dated Sep. 6, 2012.
PCT Application No. PCT/US2014/17288 International Search Report and Written Opinion dated Jun. 13, 2014.
PCT Application No. PCT/US2014/26367 International Search Report and Written Opinion dated Sep. 9, 2014.
PCT Application No. PCT/US2014/21913 International Search Report and Written Opinion dated Jun. 23, 2014.
Peter Koelln KGAA: "Kochjule, Hafer-Getrank mit Fruchtsaft", XP002499645, Internet Citation, URL:http://www.koelln.de/downloads/37/Kochjule.pdf>, retrieved from the Internet on Oct. 14, 2008, pp. 1-19, dated Oct. 14, 2008.
Peter Koelln KGAA: "Kolln Schmelzflocken Dinkel-Hafer", XP002499438, Internet Citation, URL:http:f/www.koelln.de/produkte/2/103/index.html>, retrieved from the Internet on Oct. 13, 2008, p. 1, dated Oct. 13, 2008.
Peter Koelln KGAA: "KollnFlocken Instant", XP002499437, Internet Citation, URL:http:/fwww.koelln.de/produkte/1/15/index.html>, retrieved from the Internet on Oct. 13, 2008, p. 1, dated Oct. 13, 2008.
Singh, Narpinder, et al.,""A Comparison of Wheat Starch, Whole Wheat Meal and Oat Flour in the Extrusion Cooking Process,"" J. Food Engineering 34(1997) 15-32(18 pages).

Vaclavik, Vickie A. and Elizabeth W. Christian, Springer New York, "Milk and Milk Products," Essentials of Food Science, Food Science Texts Series, pp. 237-269 (33 pages).
Tapola, N., et al.""Glycemic responses of oat brain products in type 2 diabetic patients,"" Nutrition, Metabolism & Cardiovascular Diseases (2005) 15, 255-261 (7 pages).
Anonymous: The Whole Grains Council, "What are the Health Benefits?," http://wholegrainscouncil.org/whole-grains-101/what-are-the-health-benefits, (2 pages).
Vasanthan et al., Dextrinization of Starch in Barley Flurs with Thermostable alpha-Amylase by Extrusion Cooking, vol. 53, No. 12, pp. 616-622, dated Dec. 1, 2001 (XP001110714).
Vasanthan, et al.""Dietary fiber profile of barley flour as affected by extrusion cooking,"" Food Chemistry 77 (2002) pp. 35-40 (6 pages).
"Wang, Ming-chun, et al, Extrusion Technology Applied in the Nutritional Health Foods, College of Food Engineering & Biologic Technology, Tianjin University of Science and Technology, Tianjin 300457, pp. 63-66, dated Aug. 1, 2007, with English Abstract".
Zhang Haodong, "Starch Article Technology," Jilin Science and Technology Press, Feb. 29, 2008.
Berger, R. G., "Flavours and Fragrances—Chemistry, Bioprocessing and Sustainablitiy", Springer-Verlag Berlin Heidelberg, 2007, p. 464, p. 483 (20 pages).
Encyclopedia of Food Sciences and Nutrition, 2003, 2nd ed., searched for "beta-glucan"—https://www.sciencedirect.com/topics/biochemistry-genetics-and-molecular-biology/beta-glucan (visited homepage on Aug. 16, 2018) (2 pages).
Hareland, G.A., "Evaluation of Flour Particle Size Distributionn by Laser Diffraction, Sieve Analysis and Near-Infrared Reflectance Spectroscopy," 1994, vol. 20, Issue 2, Abstract (visited homepage on Aug. 17, 2018), (1 page).
Jay, James, et al., "Modern Food Microbiology", 7th Edition, p. 123 f., Springer Science+Business Media, Inc., 2005 (23 pages).
Kent, James A., "Kent and Riegel's Handbook of Industrial Chemistry and Biotechnology," Springer Science+Business Media, LLC, 2007, vol. 1, 11th ed., pp. 1684-1685, (6 pages).
Polaina, Julio and MacCabe, Andrew, "Industrial Enzymes—Structure, Function, and Applications", Springer 2007, p. 1-34 (34 pages).
Reddy, Avanija, et al., "The pH of beverages in the United States," 2016, vol. 147, Issue 4, pp. 255-263, (10 pages).
Srilakshmi, B., "Food Science," New Age International, 2003, 3rd ed., p. 269, (5 pages).
Xiaoyan, Fu, "Optimization and comparison of the Solvent Extraction and Enzyme Assistant Extraction of Oat Phenols", Science and Technology of Food Industry, Dec. 31, 2012, vol. 33, No. 24, p. 277-281 (5 pages).
Howling, D., "Mechanisms of Starch Enzymolysis", International Biodeterioration 25, 1989, pp. 15-19, (5 pages).
Skoglund, M., "Avenanthramide Content and Related Enzyme Activities in Oats as Affected by Steeping and Germination", Journal of Cereal Science, Academic Press LTD, GB, vol. 48, No. 2, Sep. 1, 2008, pp. 294-303, XP023979477, 10 pages.

\* cited by examiner

METHOD FOR PREPARING HIGH ACID RTD WHOLE GRAIN BEVERAGES

FIELD OF THE INVENTION

The present invention relates generally to preparation of whole grain beverages. More particularly, the present invention relates to a method for preparing low viscosity whole grain flour slurry via enzymatic action, and the use of the slurry in high acid RTD beverages.

BACKGROUND

Due to high cholesterol, obesity, and heart disease concerns, many consumers are interested in making healthier choices their diets. For this reason, a need exists to provide consumers with whole grain, low cholesterol products. However, with fast-paced lifestyles, it is difficult for consumers to prepare healthy meals or snacks. Therefore, a need also exists to provide the consumer with ready-to-eat nutritious products.

Although others have attempted to make drinkable whole grain products, the texture and properties, such as sliminess, thick viscosity and mouthfeel, of the resultant products are undesirable. These undesirable characteristics are, in large part, attributable to the thick viscosity of the whole grain slurries used in preparing the products. Therefore, a need exists for a low viscosity whole grain flour slurry and method for preparing same.

Methods traditionally used in the field to reduce viscosity of whole grain flour slurries include subjecting the flour slurry to a colloid mill and adding an enzyme to the whole grain flour slurry. Both of these methods have significant drawbacks. For example, using a colloid mill to lower the viscosity of a whole grain flour slurry is extremely time consuming, as the slurry must be treated with the colloid mill for at least 45 minutes. Adding an enzyme to the flour-water slurry to reduce the viscosity is also extremely disadvantageous, as these enzymes must be purchased or manufactured at a significant cost. Moreover, the enzyme hydrolyzes the starch flour thereby modifying the structure of the flour which in turn causes the flour to lose its standard of identity as "whole grain". If the flour loses its standard of identity as "whole grain" one cannot make particular FDA-approved health claims relating to the flour.

The present invention is directed toward satisfying the need that exists in the field, for a cost-effective and time-effective method for preparing a low viscosity whole grain flour slurry. The present invention reduces the viscosity of a whole grain flour-water mixture at least ten-fold. Additionally, if used in a beverage, this reduced viscosity whole grain slurry will provide consumers with a healthy and easily consumable product with enhanced texture and drinkability.

BRIEF SUMMARY

The present invention relates to a method for preparing low viscosity whole grain flour slurry. Whole grain flour slurry with a low viscosity is useful in many applications, in particular, for use in beverages such as high acid RTD beverages.

In one aspect of the present invention, a flour-water mixture is prepared and subsequently heated, cooled, enzymatically treated to reduce the viscosity, and then acidified to lower the pH and inactivate the enzyme, to obtain a low viscosity whole grain flour slurry.

In another aspect of the present invention, the reduced viscosity whole grain flour may be added to a beverage.

DETAILED DESCRIPTION OF THE INVENTION

The present invention relates to whole grain flour slurries. In particular, the present invention relates to a method for preparing low viscosity whole grain flour slurry by heating a flour-water slurry, cooling the slurry, enzymatically treating the slurry, then acidifying the slurry to inactivate the enzyme.

The whole grain flour may be derived from oats, barley, wheat, quinoa, corn, or mixtures of these grains, although one of ordinary skill in the art would recognize that flours derived from other whole grains may also be used in accordance with the present invention. "Low viscosity" as used herein means less than 200 cP when measured at a temperature of 158° F.

In one aspect of the present invention, oat flour may be used. Typically, oat flour slurry has a particle size range of 0.02 to 2000 microns and about fifty percent of the flour slurry has a particle size of less than 91 microns. One of ordinary skill in the art would appreciate that various particle sizes may also be used.

In accordance with one aspect of the present invention, whole grain flour is added to water and mixed until the flour is fully hydrated and dispersed in the water. The water is maintained at a suitable temperature to hydrate the flour, typically 190° F. to 210° F. (87 to 99° C.), for example 195° F. (91° C.). The water and flour is generally mixed for at least 15 minutes, for example 20 minutes. This flour-water mixture may be stirred while being heated. More particularly, a Scott Turbon High Shear Mixer may be used to simultaneously stir and heat the flour-water mixture. The mixture is mixed until a viscosity of 500 to 700 cp is obtained when measured at the temperature of 70° C.

A flour to water ratio of 1:1 to 1:50 may be used to obtain the flour-water mixture. For example, the flour to water ratio may be 1:8 to 1:20 or 1:12. Any suitable amounts of flour and water are contemplated, but generally 1% to 50% whole grain flour may be added to 50% to 99% water. More specifically, 5% to 11% whole grain flour may be added to 89% to 95% water. In one aspect, 8% whole grain flour may be added to 92% water.

In accordance with another aspect of the present invention, a mixture of whole grain flours may be added to the water to form the flour-water mixture. For example, a mixture of oat, corn, quinoa, wheat and barley flours may be used. The flours may be present in various combinations and in various amounts, in accordance with the present invention.

Following hydration of the flour in water, the temperature is reduced to 120-160° F. (49-71° C.), typically 120 to 140° F. (49-60° C.) or 125 to 135° F. (52-57° C.) or 130° F. (54° C.).

An enzyme is added to the slurry to reduce the viscosity of the slurry to 40 to 60 cp. Generally, this takes 15 minutes. Viscosity is measured at 70° C. The enzyme may be any suitable enzyme to hydrolyze the starch in the oat or barley flour and does not change or adversely affect the beta-glucan that is present in the oat or barley flour. Suitable enzymes include α-amylase.

Once the desired viscosity is obtained, an acidulant is added to the flour-water mixture to inactivate the enzyme.

The acidulant should lower the pH of the flour-water mixture to less than 5, for example, 2 to 4.5 or 2.5 to 4, in particular 3 to 3.5.

The acidulant may be one or more of suitable food grade acidulants. These food grade acidulants may include phosphoric acid, citric acid, lactic acid, malic acid and tartaric acid. One of ordinary skill in the art would recognize that other food grade acidulants may also be used in the present invention. Alternatively, or in addition to, acidifying the flour-water mixture with food-grade acidulants, the mixture may also be acidified using fruit juices. Examples of fruit juices that may be used in accordance with the present invention include, but are not limited to, apple, grape, pear and citrus fruits in general.

Acidification of the flour-water mixture may take place under agitation. A high shear mixer may be used to agitate the mixture. Additionally the mixture may be agitated for a suitable amount of time to inactivate the enzyme, generally at least 15 minutes, such as 20 minutes.

Additional food-grade ingredients may also be used in accordance with the present invention. For example, colors, flavors, preservatives, buffers, proteins, sugars, stabilizers and sweeteners can be added to the low viscosity whole grain flour slurry. In addition gums such as carboxymethylcelullose (CMC), gellan gum, xanthan gum, pectin, guar gum, locust bean gum, xanthan gum, and mixtures thereof may be included in the beverage.

One of ordinary skill in the art would appreciate that the list of food-grade ingredients set forth in the immediately preceding sentence is not all-inclusive and that other food-grade ingredients may also be used in the present invention.

In another aspect of the present invention, the reduced viscosity whole grain flour slurry is added to beverages such as, but not limited to, ready-to-drink beverages, fruit juices, dairy beverages and carbonated soft drinks. This list is not all-inclusive and one of ordinary skill in the art would recognize that the slurry may be added to other beverages in accordance with the present invention.

Benefits of the present invention include a substantial reduction in time and cost to prepare a low viscosity whole grain flour slurry and a substantial reduction in the viscosity of the slurry as compared to traditional methods of reducing the viscosity of whole grain oat flour slurries. Moreover, by acidifying the flour-water mixture to obtain a low viscosity whole grain flour slurry, in accordance with the present invention, the flour is easier to process and the need for milling of the whole grain is eliminated. The low viscosity whole grain flour slurry obtained by the present invention also has desirable textural attributes such as reduced and/or eliminated sliminess, smoothness, and overall enhanced mouthfeel and texture, making it an effective and healthy addition to a beverage.

EXAMPLE

| Strawberry Banana INGREDIENTS | % | BATCH, gal 100 |
|---|---|---|
| Oat slurry | 43.0 | 171.67 kg |
| Sucrose | 7.0 | 27.95 kg |
| Strawberry flavor | 0.3 | 1.36 kg |
| Banana flavor | 0.2 | 1.01 kg |
| low acid apple juice | 5 | 19.96 kg |
| Red color 926 | 0.1 | 0.3993 kg |
| Stabilizer | 0.025 | 0.0998 kg |
|  | 0 | 0.799 kg |
|  | 0 | 0.100 kg |
| Water | 44.06 | 175.90 kg |
| TOTAL | 100 | 399.256 kg |

An oat solution is prepared with 923 kg water and 77 kg Quaker #36 by
1) Heating water to boiling;
2) Dispersing oat flour in the boiling water under high shear agitation;
3) Maintaining a hydration temperature of 200° F. for 20 minutes;
4) Recording viscosity, pH, and total solids;
5) Cooling the solution down to 130° F. after 20 minute hydration;
6) Adding enzyme at 0.05% based on oat flour weight;
7) Agitating for 15 minutes;
8) Recording viscosity, pH, and total solids;
9) Adding 0.2% phosphoric acid (85% solution) based on oat solution weight;
10) Further agitating for an additional 15 minutes;
11) Recording viscosity, pH, and total solids.

A gum solution is prepared by adding 42 gallons of 145° F. water to a kettle along with gums and then mixing the gum solution under high shear for 15 minute. The gums may be one or more of carboxylmethylcelullose (CMC), gellan gum, xanthan gum, pectin, guar gum, locust bean gum, and xanthan gum. In one example, 0.2% CMC, 0.025% xanthan, and 0.25% gellan gum is added to finished product.

A beverage is prepared by adding 171.67 kilograms of oat solution to the gum solution, adding the rest of the ingredients, adjusting the pH to 3.8 if needed, then homogenizing 3000-500 at 165 F, and processing further as needed.

As described, the present invention provides a method for preparing a low viscosity whole grain flour slurry, with beneficial attributes and various applications in the food industry and other industries.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A method for preparing a low viscosity whole grain flour slurry comprising the following steps to be performed in the order listed:
   a) dispersing whole grain flour in water at a ratio of 1:8 to 1:20 at a temperature of 87 to 99° C. to obtain a flour-water mixture;
   b) reducing the temperature of the flour-water mixture to 49-71° C.;
   c) adding alpha-amylase to reduce the viscosity of the flour-water mixture to 40 to 60 cp when measured at about 70° C., wherein alpha-amylase is the only enzyme added to the mixture; and d) acidifying the flour-water mixture to reduce the pH of the flour-water mixture to less than 5 and to obtain a low viscosity whole grain flour slurry wherein about 50 percent of the flour contained in the slurry has an average particle size of less than 91 microns.

2. The method of claim 1 wherein the pH of the flour-water mixture is reduced to 2 to 4.5.

3. The method of claim 1 wherein the pH of the flour-water mixture is reduced to 2.5 to 4.

4. The method of claim 1 wherein the flour-water mixture is dispersed using a high shear mixer.

5. The method of claim 1 wherein the flour-water mixture is acidified using at least one food-grade acidulant, at least one fruit juice, or mixtures thereof.

6. The method of claim 5 wherein the flour-water mixture is acidified using at least one food-grade acidulent selected from the group consisting of phosphoric acid, citric acid, lactic acid, malic acid, tartaric acid, and mixtures thereof.

7. The method of claim 1 further comprising the step
e) adding at least one food-grade ingredient to the low viscosity whole grain flour slurry, the at least one food-grade ingredient selected from the group consisting of sweeteners, stabilizers, preservatives, sugars, proteins, colors, flavors and mixtures thereof.

8. The method of claim 1 wherein the whole grain flour is fully dispersed in water at a ratio of 1:12.

9. The method of claim 1 wherein the whole grain flour is a mixture of whole grain flours.

10. The method of claim 9 wherein the mixture of whole grain flours is selected from the group consisting of oat, wheat, barley, corn and quinoa.

11. The method of claim 1 wherein adding an enzyme to reduce the viscosity of the slurry to 40 to 60 cp takes about 15 minutes.

* * * * *